(12) United States Patent
Uppaluri et al.

(10) Patent No.: US 6,408,046 B2
(45) Date of Patent: Jun. 18, 2002

(54) METHOD FOR DYNAMIC RANGE MANAGEMENT OF DIGITAL RADIOGRAPHIC IMAGES

(75) Inventors: Renuka Uppaluri, Pewaukee; John R. Lamberty, Oconomowoc; Ping Xue, Cottage Grove; Kenneth S. Kump; Lloyd W. Ison, both of Waukesha, all of WI (US)

(73) Assignee: General Electric Company, Waukesha, WI (US)

( * ) Notice: Subject to any disclaimer, the term of this patent is extended or adjusted under 35 U.S.C. 154(b) by 18 days.

(21) Appl. No.: 09/751,041

(22) Filed: Dec. 29, 2000

Related U.S. Application Data

(60) Provisional application No. 60/200,699, filed on Apr. 29, 2000.

(51) Int. Cl.[7] .............................................. G01N 23/04
(52) U.S. Cl. ........................................ 378/62; 378/98.8
(58) Field of Search ................................... 378/62, 98.8

(56) References Cited

U.S. PATENT DOCUMENTS 5,909,244 A * 6/1999 Waxman et al. ............ 348/222
6,127,669 A * 10/2000 Sidiropoulos et al. ... 250/208.1

* cited by examiner

Primary Examiner—David V. Bruce
(74) Attorney, Agent, or Firm—Jenkens & Gilchrist

(57) ABSTRACT

In an X-ray imaging system comprising an X-ray source, a digital X-ray detector and a display device, an arrangement is provided for setting or establishing the dynamic range of the image at the display device. The detector is operated to provide a set of count values representing X-ray image data acquired by the detector from an object of imaging, and a set of standardized values, such as optical density values, is derived from the count values. The optical density values collectively define a range of optical density values, and the dynamic range of the display device is mapped thereto. The display device is enabled to present an image of the object which appears similar to or substantially the same as an image of the object presented by, for example, a specified analog X-ray film.

20 Claims, 4 Drawing Sheets

METHOD FOR DYNAMIC RANGE MANAGEMENT OF DIGITAL RADIOGRAPHIC IMAGES

This application claims the benefit of U.S. Provisional Application No. 60/200,699, filed on Apr. 29, 2000.

BACKGROUND OF THE INVENTION

Use of digital detectors, rather than radiographic film, to acquire X-ray image data is of steadily increasing interest. However, the dynamic range of image data provided by a digital detector is typically much greater than the dynamic range of devices used to display the data, such as printers and CRT monitors. Accordingly, the dynamic range of the image data supplied by a digital detector must be mapped to the dynamic range of the monitor or other display device. This is achieved by transforming the image data by means of a look-up-table (LUT). The transformation controls the "brightness" and "contrast" of the displayed digital image, where brightness is synonymous with "window center" and contrast is synonymous with "window width". More specifically, a digital X-ray detector can be a 14-bit device, that is, each detector pixel can provide a count value, representing data, which can be any number in a range between 0 and 16,383. On the other hand, display devices of the above type are typically 8-bit devices, so that they can output only 256 different gray scale levels, from white to black. However, even if the digital detector and display had the same number of bits, it could be desirable to apply transformation to enhance visualization of the areas of interest At present, image-based techniques are commonly used to set the brightness and contrast of a digital image. For example, analysis of the histogram of a detected digital image may be used to segment the image into various areas, such as object and background. With the object identified, the mean count value in that area can be used to set the window center for display. The difference between the minimum and maximum count values in the object of interest may be used to set the window width. As is well known by those of skill in the art, the image of an object can be presented in multiple ways, by applying different transformations or LUTs to the detected data. One transformation would be a simple linear curve. More typically, the transformation would be defined by an S-curve of some form, which is generally linear along its center portion, has an associated slope, and is flattened at its ends.

Image-based techniques are highly dependent on a priori knowledge of the anatomy being imaged and on the robustness of the segmentation scheme being used. For example, image data acquired from a particular subject's lungs could be used to develop a transformation algorithm, in order to construct an LUT. The mean count value could be taken from image data at the center of the lungs, and maximum and minimum count values could represent only a region immediately surrounding the lungs. However, while the algorithm may be useful in transforming data representing an image of another subject's lungs, it would probably not be usable in connection with image data of other organs or body parts, or which represented a different background. Moreover, segmentation schemes are usually affected by the variation of count values, as well as their distribution in the image caused by the presence or absence of raw radiation, by devices such as pacemakers and collimators, and by grids.

SUMMARY OF THE INVENTION

In the invention, it has been recognized that X-ray imaging practitioners have had extensive experience in using analog X-ray film. Accordingly, the invention bases dynamic range management on a technique or procedure for acquiring X-ray image data, rather than on a particular image or object of imaging. Such method is considered to be much more adaptable to different imaging applications or requirements, and may also present images for viewing in a form which appears very similar to an analog film image.

The invention may be recited as a method for establishing or setting the dynamic range of a digital display device in an X-ray imaging system which comprises an X-ray source, a digital X-ray detector and the display device. In the method, the detector is operated to provide a set of count values representing X-ray image data acquired by the detector from an object of imaging. A specified analytical equation is applied to the set of count values, which transforms the count values to a range of standardized values. In a preferred embodiment of the invention, the standardized range of values represent optical densities. The method further comprises the step of mapping the standardized values to the dynamic range of the display device. The specified analytical function is derived from a particular count value, which uniquely corresponds to an X-ray dose required to provide a specified optical density in displaying image data on the display device. The function is further derived from the H-D curve of a specified analog film which has an associated gamma coefficient. Preferably, the specified optical density is 1.2.

DETAILED DESCRIPTION OF THE PREFERRED EMBODIMENT

In accordance with the invention, it has been recognized that X-ray imaging practitioners have extensive experience in selecting the particular analog film which will have the most suitable parameters for imaging a particular object, and which will provide an image of desired appearance. As is well known, the behavior of analog film-screen systems to exposure is characterized by a curve referred to in the art as an H-D curve. The H-D curve for a particular film is specified by a "speed" and a "gamma coefficient", wherein speed relates to the dose required to generate a pre-defined optical density. Typically, the predefined optical density is 1.2 OD, derived from the sum of 1.0 OD and a film based fog value of 0.2 OD. The gamma coefficient of the H-D curve relates to differences in optical densities produced by differences in dose.

Figure 1:
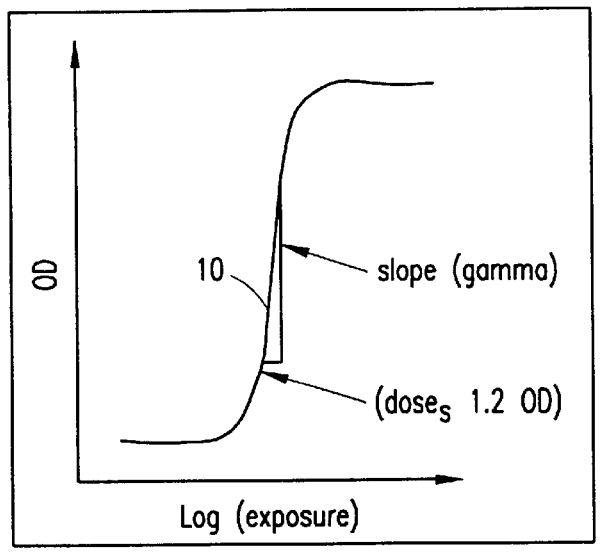
FIGS. 1–3 show different H-D curves pertaining to analog radiographic film.
Figure 2:
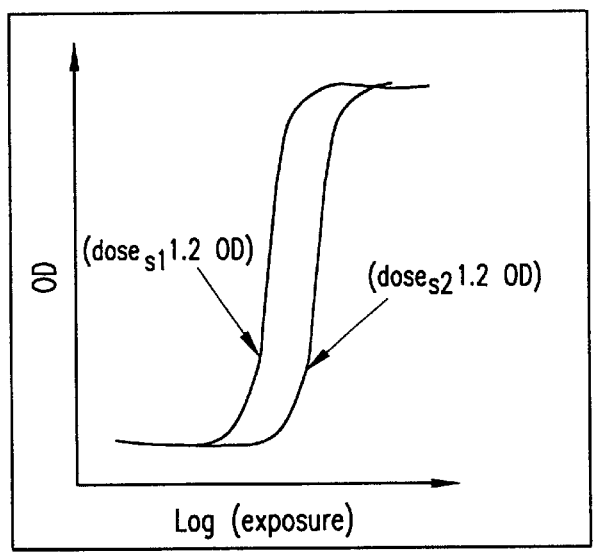
Figure 3:
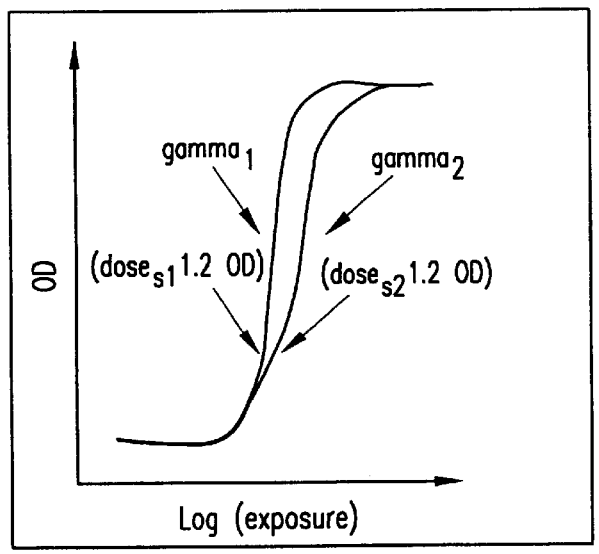

Referring to FIG. 1, there is shown the H-D curve for a specified analog film. The dose ($dose_s$) is required to produce an optical density of 1.2 OD, and thus determines the film speed. The slope of the curve, along curve portion 10, determines the gamma coefficient. FIG. 2 shows the H-D curves of two films with two different speeds, and FIG. 3 shows H-D curves of two films with different speeds and gamma coefficients.

In view of the widespread use of analog film in X-ray imaging, it would be useful to relate dynamic range management of digital display devices to analog film parameters. Such dynamic range management would thereby be based on a technique or procedure for acquiring X-ray image data, rather than on a particular image or object of imaging. Accordingly, the method would be much more adaptable to different imaging applications or requirements. Moreover, such range management method would enable a digital display device to present an image for viewing in a form that appeared very similar to an analog film image. In accordance with the method, an H-D curve is generated which is similar to the H-D curve of a corresponding analog film. However, optical density is represented as a function of count value, the parameter supplied by a digital detector, rather than as a function of exposure level, associated with analog film.

Figure 4:
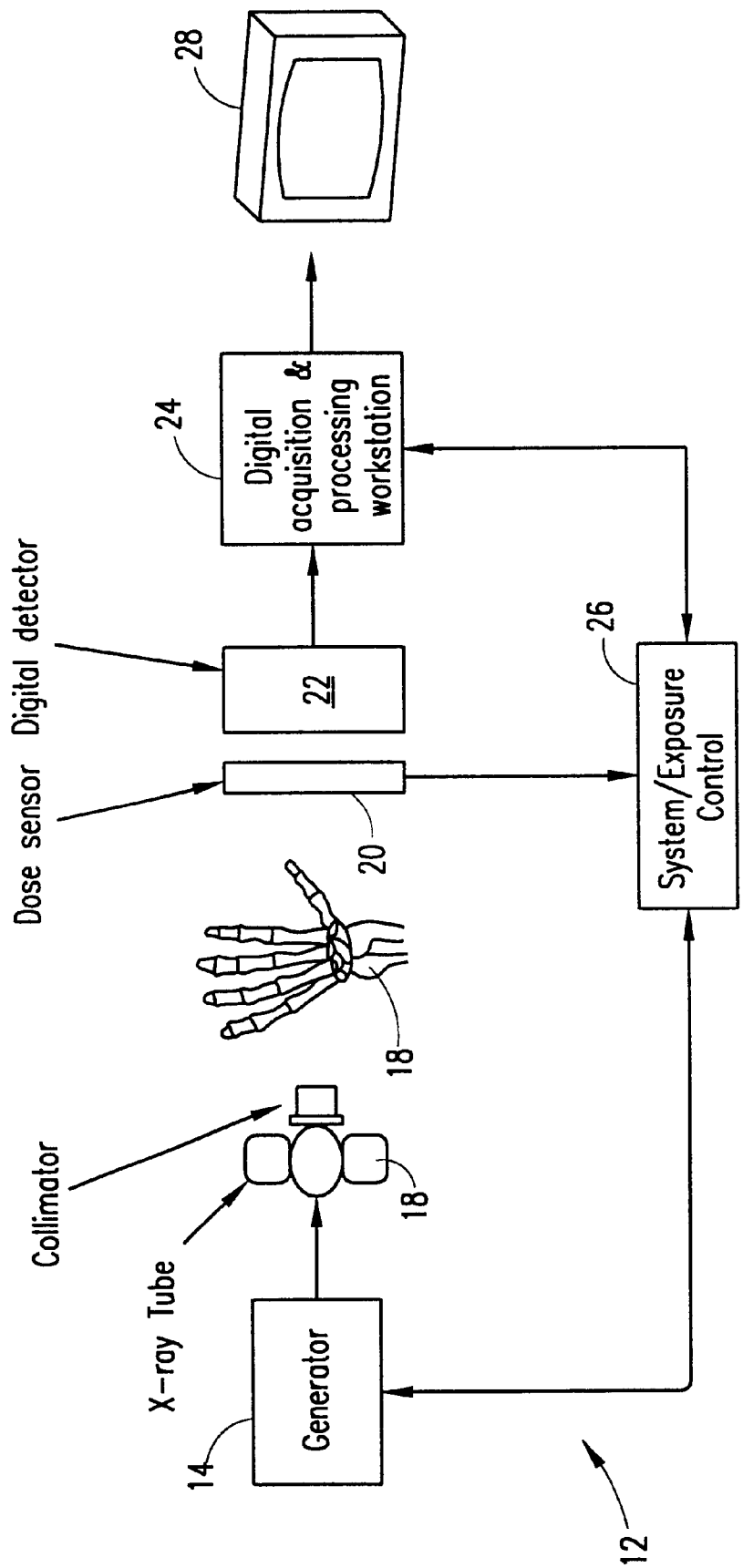
FIG. 4 is a block diagram showing an imaging system for use in connection with an embodiment of the invention.

Referring to FIG. 4, there is shown an imaging system 12 for establishing a relationship between respective parameters of an analog X-ray film and a digital X-ray detector. System 12 comprises a tube generator 14 and an X-ray tube 18 for projecting X-rays through an object of imaging 18, such as a patient's hand. System 12 further comprises a dose sensor 20, a conventional digital detector 22, a processor 24 and a system controller 26. Detector 22 detects image data, which is processed in accordance with the method described herein by processor 24, and displayed on a monitor 28 or other display device. In analog film systems a dose sensor, comprising an automatic exposure control (AEC) device, is used to measure and terminate exposure for a desired optical density. In like manner, the sensor 20 of system 12 is designed in conjunction with digital detector 22 and a feedback loop to the system controller 26, so that X-ray exposure is terminated when a pre-determined count value, corresponding to a desired optical value, is detected in the image data.

Figure 5:
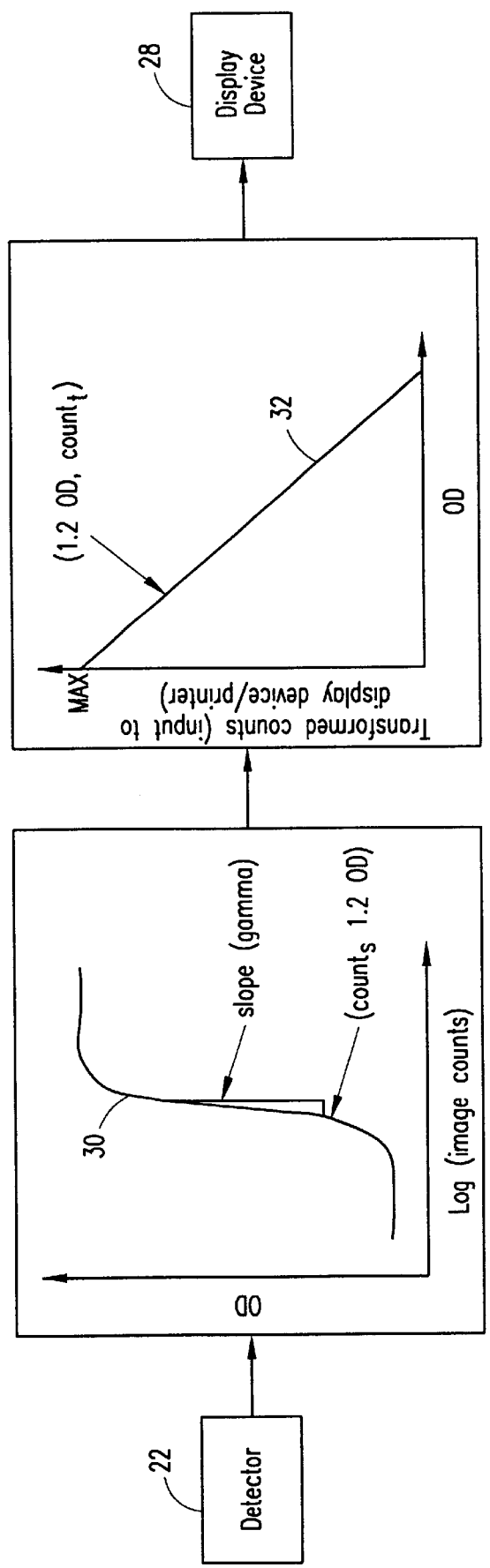
FIG. 5 is a block diagram illustrating an embodiment of the invention.

As indicated above, in analog film systems a unique dose that gives an OD of 1.2 defines the film-speed. Thus, in operating a digital detector to acquire image data in accordance with the invention, a unique count value ($count_s$), based on the unique dose, can be mapped to an OD of 1.2, and then transformed to an output count ($count_t$). This output count, when sent to a calibrated display device or printer, will achieve an OD of 1.2 in its display. Thus, $count_s$ comprises a digital "speed", which needs to be determined. Thereupon, the remaining counts in a set of detected data can be transformed, using an analytical equation representing optical density as a function of detector count value. Such analytical equation is generated from the H-D curve for the specified analog film and from count value $count_s$. Referring to FIG. 5, there is shown the analytical equation depicted as a curve 30, which is generated by the analytical equation. The slope of the curve 30, i.e., the gamma coefficient thereof, serves as another input.

Referring further to FIG. 5, there is shown curve 32, which is generated by mapping the output of curve 30 to the dynamic range of a digital display device 28. The output of curve 30 comprises a range of optical densities which are transformed by applying the function of curve 32 thereto.

As an example, in 400 speed analog film systems, a dose of 2500 nanoGy under specific conditions (e.g. energy spectrum) is required to produce an OD of 1.2. For a digital system, to produce an image equivalent to a 400 speed analog film, the dose sensor along with the system controller should be set up to terminate exposure when dose received by the detector is equal to 2500 nanoGy under similar conditions. The count value ($count_s$) on the detector produced by this dose is mapped to 1.2 OD. Knowing a digital detector transfer function (count/dose), counts can be calculated and curve 30 in FIG. 5 can be applied. The detector transfer function is determined for each digital detector by a calibration, wherein a known dose of X-radiation is applied to the detector, and the resulting count value is observed. The transformation represented by curve 32 acts as a resealing of the OD axis of curve 30 to the dynamic range of the display device 28.

The following relationship applies to this example, for count mapped to 1.2 OD for a 400 speed film look:

$$count_s = 2500 \text{ nanoGy} * \text{detector transfer function} \qquad \text{Eqn. (1)}$$

Figure 6:
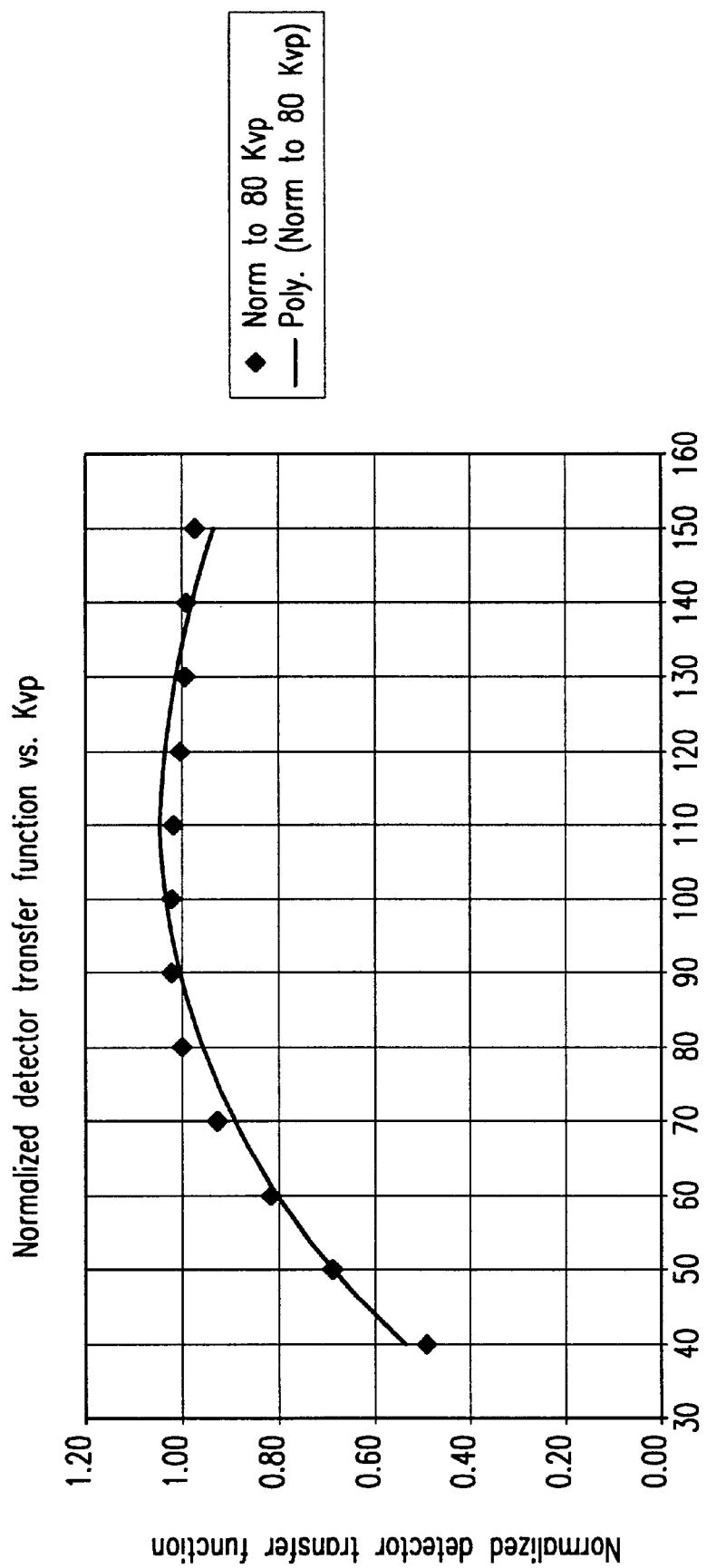
FIG. 6 is a curve showing a normalized detector transfer function plotted against Kvp.

Typically, the behavior of the dose sensor and detector transfer function is X-ray beam energy dependent. Other factors such as grid, scatter, spectral filter, and object thickness could affect the detector entrance dose measured by the dose sensor and detector transfer function. Models for dose compensation and detector transfer function could be developed based upon exposure techniques such as kVp, grid and spectral filter in or out, collimator size, etc. With the relationship between the various factors completely characterized, the mapping between dose and count can be suitably altered. For example, the detector transfer function of a digital detector varies with Kvp. The transfer function at all Kvps are normalized to the 80 Kvp value and are plotted against Kvp as shown in FIG. 6. In this situation, Equation 1 would be modified as follows:

$$count_s \text{ (mapped to 1.2 OD for a 400 speed film look)} = 2500 \text{ nanoGy} * \text{detector transfer function}/_{80Kvp} * \text{normalized detector transfer function}/_{kvp} \text{ of image aquisition} \qquad \text{Eqn. (2)}$$

The detector transfer function|80 Kvp could be periodically calibrated. All of these compensations can be provided either in software or hardware.

In some embodiments or applications, it may be desirable to apply a LUT with a shape other than the sigmoid shape of the H-D curve. In this case, the calculated count value ($count_s$) can be used as a reference point on such LUT.

Although a preferred embodiment of the method and apparatus of the present invention has been illustrated in the accompanying Drawings and described in the foregoing Detailed Description, it will be understood that the invention is not limited to the embodiment disclosed, but is capable of numerous rearrangements, modifications and substitutions without departing from the spirit of the invention as set forth and defined by the following claims.

What is claimed is:

1. In an X-ray imaging system comprising an X-ray source, a digital X-ray detector and a digital display device, a method for establishing a dynamic range for said display device comprising the steps of:

operating said detector to provide a set of count values representing X-ray image data acquired by said detector from an object of imaging;

applying a specified analytical function to said set of count values to generate a set of optical density values which collectively define an optical density range; and mapping said optical density range to the dynamic range of said display device.

2. The method of claim 1 wherein:

said specified analytical function is derived from a particular count value, which uniquely corresponds to an X-ray dose required to provide a specified optical density value.

3. The method of claim 2 wherein:

said specified analytical function is further derived from the H-D curve of a specified analog film, said H-D curve having an associated gamma coefficient.

4. The method of claim 3, wherein:
said specified optical density value is 1.2.

5. The method of claim 2, wherein:
a detector transfer function which is specifically determined for said detector is employed to derive said particular count value from said X-ray dose required to provide said specified optical density value.

6. The method of claim 5, wherein:
said detector transfer function is determined by calibration of said detector when said required X-ray dose is applied thereto.

7. The method of claim 2, wherein:
said detector is exposed to X-rays from said source as said detector acquires said image data; and
said X-ray exposure of said detector is terminated when a count value equal to said particular count value is detected in said image data.

8. The method of claim 1, wherein:
a lookup table is employed to map said optical density range to said dynamic range of said display device.

9. In an X-ray imaging system comprising an X-ray source, a digital X-ray detector and a digital display device, a method for establishing a dynamic range for said display device comprising the steps of:
acquiring a set of count values representing X-ray image data from an object of imaging;
applying a specified analytical function to said set of count values to generate a set of standardized values; and
mapping the standardized values to the dynamic range of said display device.

10. The method of claim 9, wherein:
said standardized values respectively comprise optical densities.

11. In an X-ray imaging system comprising an X-ray source, a digital X-ray detector disposed to provide count values representing detected X-radiation, and a digital display device, a method for establishing the dynamic range of said display device comprising the steps of:
initially operating said system to determine the particular count value which is provided by said digital detector when a known X-ray dose is applied thereto, said known X-ray dose being associated with a specified analog X-ray film having a corresponding H-D curve;
operating said detector to provide a set of count values representing X-ray image data acquired by said detector from an object of imaging;
deriving a functional relationship between optical density and count values from said particular count value, and from said H-D curve of said specified analog film;
applying said functional relationship to said set of count values to generate a set of optical density values which collectively define an optical density range; and
mapping said optical density range to the dynamic range of said display device.

12. The method of claim 11, wherein:
said particular count value provides a specified optical density value in displaying image data on said display device.

13. The method of claim 12, wherein:
said specified optical density value is 1.2.

14. The method of claim 11, wherein:
a lookup table is employed to map said optical density range to said dynamic range of said display device.

15. An X-ray imaging system comprising:
an X-ray source;
a digital X-ray detector disposed to provide a set of count values representing X-ray image data acquired by said detector from an object of imaging;
a digital display device coupled to said detector; and
a processor disposed to receive said count values and to generate a set of optical density values in response thereto, said optical density values being functionally related to said count values and the minimum and maximum optical density values collectively defining an optical density range, said processor being further disposed to map said optical density range to the dynamic range of said display device.

16. The system of claim 15 wherein:
said source projects X-rays toward said detector through said object to provide said image data; and
said system includes an exposure control for terminating X-ray exposure of said detector when a particular count value is detected in image data acquired thereby, said particular count value corresponding to a specified optical density value.

17. The system of claim 16 wherein:
said particular count value is associated with a specified analog X-ray film having an H-D curve, and said functional relationship between said optical density values and said count values is derived from said H-D curve and from said particular count value.

18. The system of claim 17 wherein:
said display device, in response to said set of count values, presents an image of said object which appears substantially the same as an image of said object presented by said specified analog film.

19. The system of claim 18, wherein:
said specified optical density value is 1.2.

20. The system of claim 15, wherein:
a lookup table is included in said processor for mapping said optical density range to said dynamic range of said display device.

* * * * *